United States Patent [19]

Wuts

[11] Patent Number: 4,885,404
[45] Date of Patent: Dec. 5, 1989

[54] FLURBIPROFEN INTERMEDIATE

[75] Inventor: Peter G. M. Wuts, Galesburg, Mich.

[73] Assignee: The Upjohn Company, Kalamazoo, Mich.

[21] Appl. No.: 24,300

[22] PCT Filed: Jun. 10, 1986

[86] PCT No.: PCT/US86/01275

§ 371 Date: Mar. 6, 1987

§ 102(e) Date: Mar. 6, 1987

[87] PCT Pub. No.: WO87/00519

PCT Pub. Date: Jan. 29, 1987

Related U.S. Application Data

[63] Continuation of Ser. No. 844,715 Mar. 27, 1986, abandoned, which is a continuation, of Ser. No. 754,864 July 12, 1985, abandoned.

[51] Int. Cl.[4] .................. C07C 47/796; C07C 43/243
[52] U.S. Cl. .................... 568/332; 570/128; 585/400; 548/444; 548/445; 549/12; 549/14; 549/35; 549/39; 549/72; 549/78; 549/369; 549/370; 549/430; 549/448; 562/418; 562/41; 568/58; 568/592; 568/632
[58] Field of Search .................. 570/128; 585/400; 568/632, 332

[56] References Cited

U.S. PATENT DOCUMENTS

| | | | |
|---|---|---|---|
| 3,663,584 | 5/1972 | Alvarez | 260/429.9 |
| 3,959,364 | 5/1976 | Armitage | 260/515 |
| 4,036,989 | 7/1977 | Armitage | 424/353 |
| 4,188,491 | 2/1980 | Nicholson | 562/492 |
| 4,443,631 | 4/1984 | Padilla | 564/412 |
| 4,549,025 | 10/1985 | Dalcanale | 546/327 |

FOREIGN PATENT DOCUMENTS

| | | |
|---|---|---|
| 2259243 | 6/1974 | Fed. Rep. of Germany . |
| 118605 | 3/1976 | German Democratic Rep. . |
| 53-018534 | 2/1978 | Japan . |
| 53-046943 | 4/1978 | Japan . |
| 3046943 | 4/1978 | Japan . |
| 55-127336 | 10/1980 | Japan . |
| 5127336 | 10/1980 | Japan . |
| 56-097249 | 8/1981 | Japan . |
| 6097249 | 8/1981 | Japan . |
| 6810246 | 7/1967 | Netherlands . |
| 79333 | 6/1982 | Romania . |
| 7406883 | 12/1974 | Sweden . |
| 1445283 | 8/1976 | United Kingdom . |
| 1549140 | 7/1979 | United Kingdom . |
| 1586798 | 3/1981 | United Kingdom . |

OTHER PUBLICATIONS

J. Org. Chem., 36, 2099 (1971), Ronald M. Magid et al., "The Coupling Reaction of Phenyllithium with Allylic Chlorides . . . ".

J. Org. Chem., 33, 2148 (1968), R. G. Gough et al., "Radical Mechanisms in Reactions of Grignard Reagents".

Acta Chem. Scand., 27, 888 (1973), B. O. Lindgren et al., "Preparation of Carboxylic Acids from Aldehydes . . . ".

Afinidad 40, 384 (1983).

Primary Examiner—Richard L. Raymond
Attorney, Agent, or Firm—Bruce Stein

[57] ABSTRACT

Disclosed is a process for the production of acids of the formula

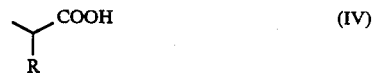

(IV)

wherein R is 2-fluoro-4-(1,1'-biphenyl), 4-(2-methylpropyl)phenyl, 6-methoxy-2-napthyl, 3-benzophenyl, 4-(2-thienylcarbonyl)-phenyl or 7-chlorocarbazole-3-yl which comprises contacting an organometallic compound of the formula R—M—$R_1$ (G) with an allyl halide of the formula

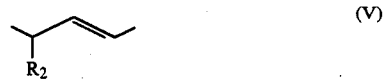

(V)

to produce an olefin of the formula

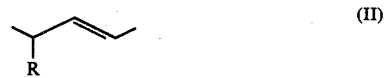

(II)

ozonolysis of the olefin (II) to produce an aldehyde of the formula

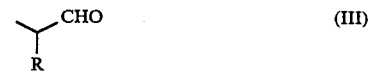

(III)

which is oxidized either directly to the acid (IV) or via a bisulfite adduct of the formula

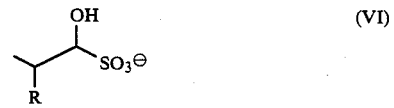

(VI)

4 Claims, No Drawings

FLURBIPROFEN INTERMEDIATE

The present patent application is the national patent application of PCT patent application 86/01275 filed 6-10-86, which is a continuation-in-part patent application of co-pending patent application Ser. No. 844,715 filed 3-27-86, now abandoned, which was a continuation-in-part patent application of co-pending patent application Ser. No. 754,864 filed 7-12-85, now abandoned.

BACKGROUND OF THE INVENTION

A number of processes to produce flurbiprofen are known, see for example, U.S. Pat. Nos. 3,959,364, 4,188,491 and 4,443,631.

The halo (I) starting materials are known, see U.S. Pat. No. 3,959,364 (column 8, lines 56–61); U.S. Pat. No. 3,959,364 (Example 9); U.S. Pat. No. 3,663,584 and Aldrich Catalog; Japanese Pat. No. 56,097,249 and Dutch Pat. No. 6,810,246 for (IA) thru (IE) respectively. The halo starting material (IF) can be prepared by methods well known to those skilled in the art. Aromatic olefins similar to the olefin (II) are known, see U.S. Pat. No. 4,036,989, more particularly Table III, Example No. 15. While that compound is isomeric with (IIA), if subjected to ozonolysis it will not produce the desired aldehyde (IIIA). Other aromatic olefins are disclosed in German Offen. 2,259,243 and Japanese Pat. No. 53,046,943. British Pat. No. 1,586,798 generically discloses the olefin (IIA); however, none of the sixteen examples sets forth any of the six olefins (IIA–IIF) of the present invention.

The aldehyde (IIIA) is known, see Japanese Pat. Nos. 55,127,336, 53,046,943 and Swedish Pat. No. 7,406,883.

The conversion of a halo compound to an aromatic Grignard reagent and its reaction with an unsaturated allylic halide is discussed in J. Org. Chem. 36, 2099 (1971), ibid 33, 2148 (1968) as well as U.S. Pat. No. 4,036,989. Prior art yields are about 75% whereas the yields of the present invention are 95 to 99%.

The ozonolysis of alkenes to the corresponding aldehydes is well known. British Pat. No. 1,586,798 discloses methods of oxidizing aromatic olefins to the corresponding acids. The British Patent discloses various oxidizing agents including ozone, and state the yield is very good.

The oxidation of an aldehyde to the corresponding acid is well known. In the present case the process is complicated by the benzylic proton which is subject to loss by over-oxidation thereby reducing the yield. Acta Chem. Scand. 27, 888 (1973) discloses the oxidation of aldehydes to acids using sodium chlorite and the requirement for a chlorine scavenger. British Pat. No. 1,445,283 describes the oxidation of biaryl aldehydes to the corresponding acids. See page 11, column 2 for the aldehyde XXXI. However, the British Patent uses standard oxidizing agents; see page 7 where various oxidizing agents are used but no mention is made of chlorite. British Pat. No. 1,549,140 discloses a process for oxidation of aromatic aldehydes to the corresponding acids by use of aqueous chlorite. However, no buffer was used, and the yields were only about 66 to about 76.5%. East German Pat. No. 118,605 discloses chlorite oxidation of 2-(4-isobutylphenyl)propionaldehyde to ibuprofen at very low pH and in only 62% yield. Japanese Kokai 53018534 discloses hypochlorite (not chlorite) oxidation of 2-(4-isobutylphenyl)propionaldehyde to ibuprofen in 82% yield without regulation of the pH. Romanian Pat. No. 79,333 discloses aqueous chlorite oxidation of 2-(4-isobutylphenyl)propionaldehyde in the presence of a chlorine scavenger to give ibuprofen in 85–90% yield. Afinidad, 384, 142–3 (1983) discloses the production of naproxen from the corresponding naproxen aldehyde by unbuffered chlorite oxidation. The process of the present invention requires a chlorine scavenger and that the pH be maintained in the range of about 4 to about 7 providing yields > 90%.

SUMMARY OF THE INVENTION

Disclosed is an olefin (II) and a bisulfite adduct (VI).

Also disclosed is a process for the preparation of the olefin (II) which comprises contacting an organometallic compound (G) with an allyl halide (V) where the allyl halide (V) and the organometallic compound (G) are contacted slowly over the period of at least 30 min.

Further disclosed is a process for the preparation of an aldehyde (III) which comprises contacting an olefin (II) with ozone in the presence of a trapping agent at a temperature of about −70° to about 10°.

Additionally disclosed is a process for the preparation of an acid (IV) in >90% chemical yield which comprises contacting an aldehyde (III) with chlorite in the presence a chlorine scavenger and water where the pH is maintained in the range of about 4 to about 7.

Also disclosed is a process for the preparation of an acid (IV) which comprises (1) contacting an aldehyde (III) with bisulfite to form a bisulfite adduct (VI), (2) contacting the bisulfite adduct (VI) with an agent selected from the group consisting of chlorite in the presence of water at a pH of from about 6 to about 7, or with DMSO and an anhydride.

Further disclosed is a process for the preparation of an acid of formula (IV) which comprises (1) contacting an olefin of formula (II) with ozone in the presence of a trapping agent at a temperature of about −70° to about 10° and (2) contacting the aldehyde (III) with chlorite in the presence of water.

DETAILED DESCRIPTION OF THE INVENTION

The halo (I) starting materials are well known to those skilled in the art or can be readily prepared from known compounds by methods well known to those skilled in the art. See, for example, U.S. Pat. No. 3,959,364 (column 8, lines 56–61); U.S. Pat. No. 3,959,364 (Example 9); U.S. Pat. No. 3,663,584 and Aldrich Catalog; Japanese Pat. No. 56,097,249; and Dutch Pat. No. 6,810,246; for (IA) thru (IE) respectively. It is preferred that R be 2-fluoro-4-(1,1'-biphenyl) (A), 4-(2-methylpropyl)benzene (B), or 6-methoxy-2-naphthyl (C). It is more preferred that R be 2-fluoro-4-(1,1'-biphenyl). It is preferred that $R_1$ be a chlorine or bromine atom; it is more preferred that $R_1$ be a bromine atom.

The halo compound (I) is converted to the corresponding organometallic compound (G) by reaction with a metal (M) as is well known to those skilled in the art. It is preferred that (M) is magnesium. The organometallic compound (G) is then contacted with an allyl halide (V) to give the olefin (II). It is preferred that the allyl halide (V) be allyl chloride. Similar coupling reactions of aryl magnesium halides with allylic halides are known and give yields generally about 75%. The process of the present invention gives yields which are much higher. Dry ether solvents are suitable for the process of forming the olefin (II) as is well known to those skilled in the art. The reaction may be performed at a temperature up to about 80°, however about −10° to about 25° is preferred. While it is desirable to know the quality of the allyl halide (V) it is not necessary. If the allyl halide is pure, one equivalent is sufficient; however, to be safe in case the allyl halide is not pure it is recommended that 1.2 to 1.5 equivalents of the allyl halide (V) be used. It is necessary to contact the allyl halide (V) and the organometallic compound (G) slowly, over a period of at least 30 min, preferably over a period of 1 to 3 hr. The allyl halide (V) can be added to the organometallic compound (G) or the organometallic compound (G) can be added to the allyl halide (V); what is important is the rate of contacting.

An alternative process to produce the olefin (II) comprises contacting the organometallic compound (G) with the allyl halide (V) in the presence of a nickel catalyst (VIII). It is preferred that $A_1$ and $A_2$ are both chlorine atoms and $L_1$ and $L_2$ are either $\phi_3 P$ or $[\phi_2 P—(CH_2)_m—P\phi_2]$ where m is 2 or 3.

Another similar process to produce the olefin (II) comprises contacting the halo compound (I) with a olefinic Grignard reagent of formula (VII), in the presence of the nickel catalyst (VIII). It is preferred that $A_1$ and $A_2$ are both chlorine atoms and $L_1$ and $L_2$ are either $\phi_3 P$ or $[\phi_2 P—(CH_2)_m—P\phi_2]$ where m is 2 or 3.

Another process to produce the olefin (II) comprises contacting the allyl halide (V) with the halo compound (I) in the presence of a Nickel catalyst selected from the group consisting of $Ni(CO)_4$ or $Ni(cyclooctadiene)_2$. With this reaction it is preferred that the solvent be DMF.

When the halo compound (I) contains a ketone function as the halo compounds (ID and IE) these carbonyl groups must be protected as is well known to those skilled in the art. See for example, Protecting Groups in Organic Synthesis, Theodora W. Greene, Wiley-Interscience, New York, 1981, Chapter 4. The protected forms are set forth in CHART D as (ID/IE-O) and (ID/IE-C). The ketone function must be protected during the Grignard reaction producing the olefin (II) as is well known to those skilled in the art. The ketone functionality need not be protected during the ozonolysis of the olefin (II) to the aldehyde (III) or the oxidation of the aldehyde (III) to the acid (IV). The protecting group is removed when desired by means well known to those skilled in the art.

Ozonolysis of alkenes to aldehydes is well known to those skilled in the art. One equivalent of ozone is required, 1-2 equivalents are operable and 1.0 equivalents are preferred. The scientific literature regarding ozonolysis teaches that the reaction should be performed in the cold, usually at dry ice temperatures of about −60°. The process of the present invention is be performed at temperatures from about −70° to about 10°; more preferably about −60° to about −30°. If one performs the ozonolysis in the absence of a trapping agent one might obtain an ozonide which probably will irreversibly decompose, while if one performs the same ozonolysis in the presence of a trapping agent, one obtains the hydroperoxide, as is well known to those skilled in the art. Trapping agents are of the formula Z—OH and include alcohols (Z is alkyl), water (Z is a hydrogen atom) and acids (Z is $R_{11}$—CO). The hydroperoxide is advantageous over the ozonide because it is more stable; the ozonide is more likely to decompose. If the trapping agent is an alcohol, the alcohol can be used as the solvent but preferred is a mixture of alcohol and a halogenated hydrocarbon such as methylene chloride. Virtually all alcohols in which the reactant is soluble are operable. When the trapping agent is an alcohol it is preferred that the alcohol be selected from the group consisting of methyl, ethyl alcohol or t-butyl alcohol. It is preferred that the trapping agent be an acid, more preferably acetic acid. One equivalent of the trapping agent is needed. It is preferred that greater than one equivalent of trapping agent be present. When the trapping agent is an acid and the reducing agent is zinc, two equivalents of the trapping agent are required. Following completion of the ozonolysis the reaction mixture is contacted with a reducing agent. Suitable reducing agents include dimethylsulfide, zinc and acetic acid, aqueous sodium bisulfite, sodium dithionite, trimethylphosphite, triethylamine and equivalents thereof. Preferred are dimethylsulfide, trimethylphosphite and zinc/acetic acid; most preferred is zinc/acetic acid. At least one equivalent of reducing agent is needed, it is preferred that 1-2 equivalents of reducing agent be used. Because of the benzylic proton, even in view of the prior art teachings of yields in the range of about 90%, it was expected the yields of the present process would be significantly lower. Therefore, it is surprising that the ozonolysis process gives yields of 90%, at temperatures of up to about 0°.

The conversion of an aldehyde to the corresponding acid by oxidation is well known to those skilled in the art. With oxidation of aldehydes which do not have a benzylic proton it is known that one skilled in the art should be able to obtain yields (chemical) of about 75 to about 95%. However, when one oxidizes an aldehyde with a benzylic proton one skilled in the art would expect a considerably lower yield because of the ease of over-oxidation in a reaction such as the oxidation reaction of the present invention. Numerous oxidizing agents well known to those skilled in the art were tried to convert the aldehyde (III) to the acid (IV). These oxidizing agents produced the acid (IV) in yields of less than 60%. This was not unexpected in view of the benzylic proton. However, when chlorite is used as the oxidizing agent in the presence of a chlorine scavenger and water and the pH is maintained in the range of pH 4 to 7 the yields are much higher. It is preferred to use at least 1 equivalent of chlorite. It is more preferred that 1.5 to 2.0 equivalent be used. The nature of the chlorite cation is not particularly important but sodium and potassium are preferred as it is preferred that the oxidizing agent be in solution and sodium and potassium chlorite are very water soluble. The reaction proceeds with just chlorite and water but the yields are much lower. For excellent yields it is necessary to maintain the pH between about 4 and about 7 and use a chlorine scavenger. The reaction is operable with the pH in the range of 2 to 8; below 2 the reaction is hazardous. It is preferred to maintain the pH in the range of about 4 to about 7, more preferably in the range of about 6 to about 7. It is preferred to maintain the pH in the desired range by use of a buffer. The exact chemical composition of the buffer is not important; what is important is that the pH be maintained from about 4 to about 7. Preferable buffers include phosphate, borate, acetate or carbonate, and equivalents thereof with sufficient buffer capacity to maintain the pH <8 during the reaction. It is preferred that the buffer be phosphate. The chlorine scavenger is selected from the group consisting of sulfamic acid, an olefin, polyolefinic compound or peroxide. Preferred chlorine scavengers include sulfamic acid, butene, cyclohexene, 2,3-dimethylbutene, 2-methylbutene, hydrogen peroxide, t-butylhydrogen peroxide and equivalents thereof. The most preferred chlorine scavenger is sulfamic acid. It is preferred that at least 1 equivalent of the chlorine scavenger be used, more preferably 1.2 to 1.6 equivalents. With the butenes the position of the double bond is not important. It is preferable to perform the process in the presence of a phase transfer catalyst is of the formula $R_7R_8R_9R_{10}N+$ where the nature of the anion is not important. The phase transfer catalyst is not absolutely necessary but does provide for a better yield and better quality product, if a chlorine scavenger is used, and is preferably selected from the group consisting of tributylmethyl ammonium chloride and tetrabutylammonium sulfate. The reaction requires some water and while it is not necessary it is preferred to use sufficient water to dissolve the oxidizing agent. The reaction can be performed in a temperature range of about 0 to about 40°, however, about 5 to about 15° is preferred. While the oxidant, chlorite, can be added to the aldehyde (III), it is preferred to add the aldehyde (III) to the oxidant. The above process produces the acid (IV) in chemical yields >90%, preferably >92%, more preferably >94%.

An alternative process for transforming the aldehyde (III) to the acid (IV) is by first forming a bisulfite adduct (VI). This adduct is a solid and can readily be used to purify the aldehyde (III). The nature of the cation is not important. Suitable cations include sodium, potassium, calcium, magnesium, lithium, barium, cesium or tetraalkylammonium where the alkyl portion is from 1 thru 20 carbon atoms. The bisulfite adduct is then oxidized to the corresponding acid (IV) either (1) by chlorite as described above with the exception that the pH be maintained in the range of about 6 to about 7 rather than the range of about 4 to about 7, or (2) with DMSO and an anhydride. While the nature of the anhydride is not critical anhydrides of the formula $R_a$—CO—O—CO—$R_b$ are preferred. More preferred are anhydrides selected from the group consisting of acetic anhydride, trifluoroacetic anhydride, trichloroacetic anhydride and propionic anhydride.

The acids (IV) are known to be useful pharmaceutical agents: (IVA) is flurbiprofen, see U.S. Pat. No. 3,755,427; (IVB) is ibuprofen, see U.S. Pat. Nos. 3,228,831 and 3,385,886; (IVC) is naproxen, see U.S. Pat. No. 3,637,767; (IVD) is ketoprofen; see U.S. Pat. No. 3,641,127; (IVE) is suprofen, see German Pat. No. 2,353,357; (IVF) is carprofen, see U.S. Pat. No. 3,896,145.

DEFINITIONS

The definitions and explanations below are for the terms as used throughout the entire patent application including both the specification and the claims.

All temperatures are in degrees Centigrade.

TLC refers to thin-layer chromatography.

THF refers to tetrahydrofuran.

DMSO refers to dimethylsulfoxide.

DMF refers to dimethylformamide.

Saline refers to an aqueous saturated sodium chloride solution.

When solvent pairs are used, the ratios of solvents used are volume/volume (v/v).

When the term "alkyl of—thru—carbon atoms" is used, it means and includes isomers thereof where such exist.

MTBE refers to methyl t-butyl ether.

$\phi$ refers to phenyl.

Allyl chloride refers to 4-chloropent-2-ene.

Flurbiprofen refers to 2-[2-fluoro-4-(1,1'-biphenyl)propionic acid.

Ibuprofen refers to 2-(4-isobutylphenyl)propionic acid.

Sulfamic acid refers to $NH_2SO_3H$.

Chlorite refers to $ClO_2^-$.

$A_1$ and $A_2$ are the same or different and are selected from the group consisting of a chlorine, bromine or iodine atom, —$OR_3$ or $R_3$—CO— group or (W), identified in CHART D.

G is an oxygen or sulfur atom.

$L_1$ and $L_2$ are the same or different and are selected from the group consisting of —$PR_3$, —$P(OR_3)_3$, $(R_3O)_2P$—$(CH_2)_n$—$P(OR_3)_2$ and $(R_3)_2P$—$(CH_2)_m$—$P(R_3)_2$.

M refers to magnesium, manganese, cadmium, zinc, copper, lithium or cesium.

Q is an oxygen or sulfur atom.

R is selected from the group consisting of the compounds set forth in CHART C.

$R_1$ is a chlorine, bromine, or iodine atom.

$R_2$ is a fluorine, chlorine, bromine, iodine atom or methoxy group.

$R_3$ is $C_1$-$C_5$ alkyl or phenyl.

$R_4$ is $C_1$-$C_5$ alkyl or phenyl.

$R_5$ is a methyl or ethyl group.

$R_6$ is a methyl or ethyl group.

$R_7$, $R_8$, $R_9$ and $R_{10}$ are the same or different and are $C_1$-$C_{20}$ alkyl.

$R_{11}$ is $C_1$-$C_5$ alkyl.

$R_a$ is $C_1$-$C_5$ alkyl substituted with 0 thru 3 fluorine or chlorine atoms.

$R_b$ is $C_1$-$C_5$ alkyl substituted with 0 thru 3 fluorine or chlorine atoms.

Z is $C_1$-$C_5$ alkyl, a hydrogen atom or $R_{11}$—CO.

a is 2 or 3.

m is 1 thru 4.

n is 1 thru 4.

When the term "$C_x$-$C_y$ alkyl" is used, it means an alkyl group of x thru y carbon atoms and includes isomers thereof where such exist.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

4-[2-fluoro-4-(1,1'-biphenyl)]pent-2-ene (IIA)

4-Bromo-2-fluoro-1,1'-biphenyl (IA, 25.0 g), magnesium (3.0) and THF (150 ml) are mixed at about 10°–15° for 2 hr under nitrogen. After formation of the Grignard, allyl chloride (22 ml) is added slowly via a syringe over a period of 1.5 hr. The reaction is stirred an additional 2 hr and worked up by pouring into water and extracting the MTBE. The extract is dried, concentrated to give the title compound.

EXAMPLE 2

2-[2-Fluoro-4-(1,1'-biphenyl)]propanal (IIIA)

4-[2-Fluoro-4-(1,1'-biphenyl)]pent-2-ene (IIA, Example 1, 1.0 g) is dissolved in methanol (5 ml). Methylene chloride (15 ml) and Sudan 3 are added. Ozone is bubbled thru the mixture until the color disappears. The reaction temperature is maintained at $-10°$. Trimethylphosphite (1 ml) is added and the temperature rises to about 0°. After 5 min, hydrochloric acid (5%, 10 ml) is added and the temperature rises to about 10°. The reaction mixture is stirred for about 5 min and then worked up with methylene chloride to give the title compound.

For purification, the title compound is taken up in MTBE, washed with water, dried, and concentrated to give purified title compound.

EXAMPLE 3

Flurbiprofen (IVA)

The 2-[2-fluoro-4-(1,1'-biphenyl)]propanal (IIIA, Example 2) is dissolved in THF (200 ml), cooled to 10° and treated with a mixture prepared from disodium hydrogen phosphate (19.0 g), sulfamic acid (11.6 g) and sodium hypochlorite (11.6 g) in water (300 ml). The temperature of the mixture rises to 30°. When the addition is complete the ice bath is removed and the mixture is stirred for 1 hr and then poured into MTBE (200 ml). The aqueous phase is removed and the organic phase is washed with water (100 ml) and then saline (100 ml). MTBE and the THF are removed under vacuum and the product crystallized from methanol/water (1/1; 400 ml) to give the title compound. The mother liquors are concentrated, taken up in MTBE and washed with potassium hydroxide (10%). The basic mixture is acidified with concentrated hydrochloric acid and the flurbiprofen is isolated with MTBE and crystallized from acetic acid/water (1/1) to give additional title compound.

EXAMPLES 4-10

Transformation of 4-bromo-2-fluoro-1,1'-biphenyl (IA) to 4-[2-fluoro-4-(1,1'-biphenyl)]pent-2-ene (IIA)

Following the general procedure of Example 1 and making non-critical variations but making the changes of Column B, 4-bromo-2-fluoro-1,1'-biphenyl (IA) is transformed to 4-[2-fluoro-4-(1,1'-biphenyl)pent-2-ene (IIA).

| Column A (Example) | Column B (Change) |
| --- | --- |
| 4 | T = 8-12°; a two fold excess of allyl chloride added over 1.5 hr |
| 5 | Same as Example 4 |
| 6 | Slow addition of different source allyl chloride |
| 7 | Slow addition of old allyl chloride; new source of 4-bromo-2-fluoro-1,1'-biphenyl (I) |
| 8 | Same as Examples 4 and 5 |
| 9 | Same as Examples 4 and 5 |
| 10 | Same as Examples 4 and 5 |

EXAMPLES 11-13

Transformation of 4-[2-fluoro-4-(1,1'-biphenyl)]pent-2-ene (IIA) to 2-[2-fluoro-4-(1,1'-biphenyl)]propanal (IIIA)

Following the general procedure of Example 2 and making non-critical variations but making the changes of Column D, 4-[2-fluoro-4-(1,1'-biphenyl)]pent-2-ene (IIA) is transformed to 2-[2-fluoro-4-(1,1'-biphenyl)]-propanal (IIIA).

| Column C (Example) | Column D (Change) |
| --- | --- |
| 11 | T = $-37$ to $-41°$; reducing agent is dimethylsulfide |
| 12 | T = $-17$ to $-23°$; reducing agent is dimethylsulfide |
| 13 | T = about $-40°$ |
| 14 | T = $-33$ to $-42°$; reducing agent is dimethylsulfide |

EXAMPLES 15-20

Transformation of 2-[2-fluoro-4-(1,1'-biphenyl)]propanal (IIIA) to flurbiprofen (IVA)

Following the general procedure of Example 3 and making non-critical variations but making the changes of Column F, 2-[2-fluoro-4-(1,1'-biphenyl)]-propanal (IIIA) is transformed to flurbiprofen (IVA).

| Column E (Example) | Column F (Change) |
| --- | --- |
| 15 | T = 20-25° |
| 16 | T = 10° ± 2°; stir one hr |
| 17 | T = 0° |
| 18 | T tried $-10°$; froze; about 0° |
| 19 | No chlorine scavenger |
| 20 | No buffer |

EXAMPLE 21

2-[2-Fluoro-4-(1,1'-biphenyl)]propanal bisulfite adduct (VIA)

Sodium bisulfite (5.502 g) in water (10 ml) is added slowly to 2-[2-fluoro-4-(1,1'-biphenyl)]propanal (IIIA, 3.004 g) in methanol (30 ml) and permitted to stir for 60-70 hr. The mixture is filtered, the round bottom flask and the cake are washed with MTBE. The cake is vacuum dried overnight to give the title compound. The filtrate is concentrated to dryness and dried under vacuum overnight to give additional title compound.

EXAMPLE 22

Flurbiprofen (IVA)

2-[2-Fluoro-4-(1,1'-biphenyl)]propanol bisulfite adduct (VIA, 2.66 g), acetic anhydride (5.4 ml) and DMSO (11.5 ml) are stirred at 20°-25° for 48 hr. Sodium hydroxide is added until the reaction mixture becomes basic and then stirred. The reaction is then poured in to hydrochloric acid (10%) and the product isolated with MTBE to give crude title compound. The crude material is purified by crystallization from MTBE/hexane to give purified title compound.

EXAMPLE 23

Flurbiprofen (IVA)

2-[2-Fluoro-4-(1,1'-biphenyl)]propanal bisulfite adduct (VIA) is taken up in THF (150 ml) and water (150 ml) and treated with a mixture of sodium hydrogen phosphate (40 g), sulfamic acid (24 g), sodium chlorite (30 g) and water (150 ml). The temperature is kept <20°. After the items are combined, they are stirred for 1 hr. MTBE is added, the phase separated, and the MTBE is concentrated. The concentrate is taken up in MTBE/heptane (1/1, 150 ml) and treated with piperidine (10 ml) to precipitate the salt. The salt is filtered, washed with MTBE, acidified with sulfuric acid (10%) and the product is isolated with MTBE. The product is crystallized from ethyl acetate/heptane (13/87, 150 ml) to give the title compound.

EXAMPLE 24

Flurbiprofen (IVA), One Pot Process Via the Aldehyde (III)

4-[2-Fluoro-4-(1,1'-biphenyl)]pent-2-ene (IIA) in t-butyl alcohol (200 ml) and methanol (20 ml) containing Sudan III is ozonized at −10° to −12° until the Sudan III color is gone. After the ozonolysis the reaction mixture is warmed to 0° and treated with a solution of sodium chlorite (25 g), sodium phosphate (50 g), sulfamic acid (17.5) and water (300 ml) maintaining the temperature at <10° for 1 hr. TLC shows the reaction is complete. The product is isolated by extraction with MTBE after addition of water (3×200 ml). Charcoal is added and the mixture filtered, the filtrate is concentrated to give a solid. The solid is recrystallized from ethyl acetate/hexane (13/87) to give the title compound.

EXAMPLE 25

Ibuprofen (IVB)

Following the general procedure of Examples 1 thru 3 and making non-critical variations but starting with 1-bromo-4-(2-methyl)propylbenzene (IB) the title compound is obtained.

EXAMPLE 26

Naproxen (IVC)

Following the general procedure of Examples 1 thru 3 and making non-critical variations but starting with 2-bromo-6-methoxynaphthalene (IC) the title compound is obtained.

EXAMPLE 27

Flurbiprofen (1VA)

4-[2-Fluoro-4-(1,1'-biphenyl)]pent-2-ene (IIA, Example 1, 22.17 g) is dissolved in methylene chloride (300 ml) and acetic acid (14.2 ml) and ozonized at about −55° to −50° until the Sudan 3 color disappears followed by sparging with nitrogen. A slurry is formed of water (80 ml) and zinc dust (69 g). The solution of the aldehyde at about 0° to −5° is added quickly (about 3 min) to the zinc slurry. Additional zinc dust (1.16 g) is added since the mixture indicated peroxide positive. The mixture is permitted to warm to about 15° to about 20°. 0.9 g of additional zinc dust are added and the temperature rises to about 23° without cooling. The mixture is filtered thru celite 545 (6 g) using methylene chloride for transfers. The methylene chloride layer is removed in a separatory funnel. The aqueous phase is back extracted with methylene chloride (50 ml). The organic phase is washed with water (100 ml) and the wash is back extracted with the same methylene chloride as before. The organic phases are combined and concentrated under reduced pressure to an oil. The oil is dissolved in MTBE (100 ml) and 2-methyl-2-butene (26 ml). A mixture containing water (80 ml), dipotassium hydrogen phosphate (3.4 g), potassium dihydrogen phosphate (3.4 g) and tributylmethylammonium chloride (1.25 g) is added followed by an aqueous sodium chloride solution (25%, 40 ml). Ice is added to the water bath to keep the temperature <26°, maintaining the temperature in the range of 17°–26°. TLC after 35 min shows the reaction to be done. Sodium hydrogen sulfite (NaHSO$_3$, 20 g) in a total of 100 ml of solution is added with ice bath cooling keeping the temperature under 25°. The potassium iodide test shows the residual oxidant is quenched. The mixture is worked up by extracting the MTBE layer with water (100 ml) containing potassium hydroxide (20%) followed by water (100 ml) containing potassium hydroxide (2%). The aqueous extracts are combined and acidified with hydrochloric acid (37%, 20 ml). The mixture is extracted with methylene chloride (2×100 ml). The extracts are combined and concentrated to an oil which solidifies on standing. Acetic acid (60 ml) is added, the mixture dissolved, cooled on a ice bath. Water (70 ml) is added to precipitate the solids and the slurry stirred for 15 min and filtered to give the title compound.

EXAMPLE 28

2-[2-Fluoro-4-(1,1'-biphenyl)]propanal (IIIA)

4-[2-Fluoro-4-(1,1'-biphenyl)]pent-2-ene (IIA, 48.0 g) is dissolved in methylene chloride (300 ml) and acetic acid (32 ml). The mixture is cooled to about −55° and a mixture of ozone and oxygen is sparged thru at a rate of 2 standard l/min. The reaction is monitored by TLC. After about 96 min the ozone is replaced by nitrogen sparging for 8 min. The reaction mixture at about −50° is then added to a slurry of zinc (18 g) and water (350 ml) under exothermic conditions with the temperature rising to about 38°. The reaction is checked by TLC and peroxide test paper. The slurry is filtered thru celite (10 g) using a 150 ml "C" glass filter. The mixture is transferred to a separatory funnel, the layers separated and the organic phase washed with water (350 ml). The zinc cake is washed with methylene chloride (100 ml). The original aqueous phase is back extracted and discarded. The aqueous wash is back extracted and added to the methylene chloride zinc wash. The organic phases are combined, dried and concentrated to give the title compound.

EXAMPLE 29

Flurbiprofen (IVA)

2-[2-Fluoro-4-(1,1'-biphenyl)]propanal (IIIA, Example 28, 18.65 g) is added over 30 min to a mixture of dipotassium phosphate (28 g), sulfamic acid (11 g), sodium chlorite (15 g), water (100 ml) and THF (60 ml) precooled to 10°. During the addition the pot temperature is kept at 10°±2°. The reaction is complete after 30 min as measured by TLC. Sodium bisulfite (13 g) and water (50 ml) are added all at once with the temperature rising to 30°. The layers are separated. The aqueous layer is backwashed, then discarded combining the organic phases. Potassium hydroxide (9%, 100 ml) is added to the organic phases. The THF is then removed on a rotary evaporator. The mixture is filtered and the filtrate back-extracted with isooctane (50 ml). Hydrochloric acid (15 ml) is added to the aqueous phase after separation. The aqueous phase is then extracted 2× with butyl chloride (250 ml and 100 ml). The organic phases are combined and filtered thru silica gel slowly. The filtrate is concentrated to 120 ml. Heptane (120 ml) is added and the mixture again concentrated to 120 ml. Heptane (120 ml) is added to the slurry, again concentrated to 120 ml and stirred in an ice bath (about 5°). The mixture is filtered, the filter cake washed and dried to give the title compound.

EXAMPLE 30

Flurbiprofen (IVA)

Following the general procedure of Example 29 and making non-critical variations the title compound is obtained in >90% chemical yield.

EXAMPLE 31

Flurbiprofen (IVA)

Following the general procedure of Example 29 and making non-critical variations the title compound is obtained in >92% chemical yield.

EXAMPLE 32

Flurbiprofen (IVA)

Following the general procedure of Example 29 and making non-critical variation the title compound is obtained in >94% chemical yield.

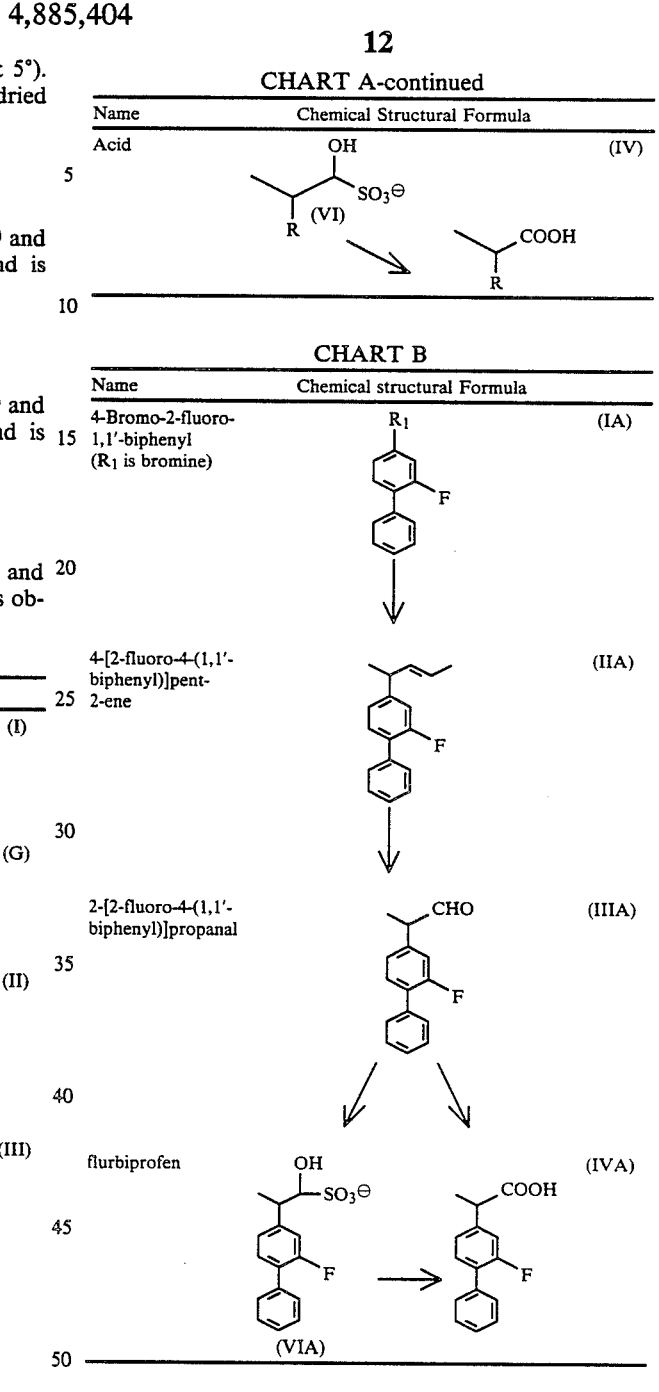

CHART C-continued

| Name | R is selected from the group consisting of Chemical Structural Formula | |
|---|---|---|
| 4-(2-methylpropyl)phenyl | 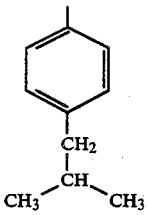 | (B) |
| 6-methoxy-2-napthyl | 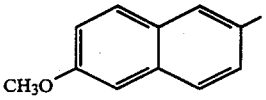 | (C) |
| 3-benzoylphenyl | 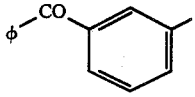 | (D) |
| 4-(2-thienylcarbonyl)-phenyl | 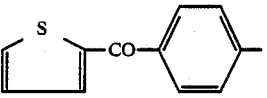 | (E) |
| 7-chlorocarbazole-3-yl | 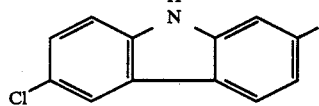 | (F) |

CHART D

| Name | Chemical Structural Formula | |
|---|---|---|
| Olefinic Grignard | 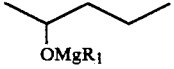 | (VII) |
| Nickel catalyst | $NiA_1A_2L_1L_2$ | (VIII) |
| | 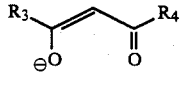 | (W) |
| allyl halide | 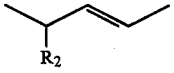 | (V) |
| | 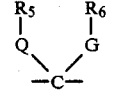 | (ID/IE-O and IID/IIE-O) |

CHART D-continued

| Name | Chemical Structural Formula | |
|---|---|---|
| | 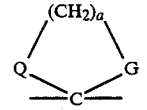 | (ID/IE-C and IID/IIE-C) |

I claim:

1. An olefin of the formula (II)

where R is selected from the group consisting of 3-fluoro-4-phenylphenyl (A), 4-(2-methylpropyl)phenyl (B), 6-methoxy-2-naphthyl (C) and 3-benzoylphenyl (D) and carbonyl protected forms of (IID).

2. An olefin according to claim 1 where R is 2-fluoro-4-(1,1'-biphenyl) (A) which is 4-[2-fluoro-4-(1,1'-biphenyl)]pent-2-ene.

3. An olefin according to claim 1 where R is 4-(2-methylpropyl)-phenyl (B).

4. An olefin according to claim 1 where R is 6-methoxy-2-naphthyl (C).

* * * * *